United States Patent

Coussediere

[11] 4,273,771
[45] Jun. 16, 1981

[54] NOVEL $\Delta^{4,9}$-GONADIENE-21-OL-3,20-DIONES

[75] Inventor: Daniel Coussediere, Montfermeil, France

[73] Assignee: Roussel Uclaf, Paris, France

[21] Appl. No.: 55,019

[22] Filed: Jul. 5, 1979

[30] Foreign Application Priority Data

Jul. 13, 1978 [FR] France .................. 78 20973

[51] Int. Cl.³ .................. C07J 71/00; A61K 31/56
[52] U.S. Cl. .................. 424/242; 260/239.55 C; 260/397.47
[58] Field of Search .................. 260/239.55 C, 397.47; 424/243, 242

[56] References Cited

U.S. PATENT DOCUMENTS

| | | | |
|---|---|---|---|
| 3,679,714 | 7/1972 | Warnant et al. | 260/397.3 |
| 3,810,885 | 5/1974 | Bucourt et al. | 260/397.4 S |

Primary Examiner—Elbert L. Roberts
Attorney, Agent, or Firm—Hammond & Littell, Weissenberger and Muserlian

[57] ABSTRACT

Novel $\Delta^{4,9}$-gonadiene-21-ol-3,20-diones of the formula

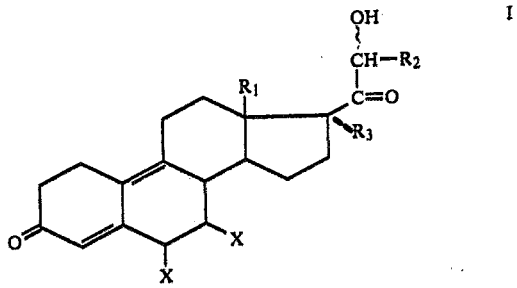

wherein X is selected from the group consisting of hydrogen and tritium, $R_1$ is alkyl of 1 to 3 carbon atoms, $R_2$ is alkyl of 1 to 12 carbon atoms and $R_3$ is alkyl of 1 to 4 carbon atoms in the form of 21R or 21S epimers or mixtures thereof having progestomimetic and antiestrogenic properties, their preparation and novel intermediates.

24 Claims, No Drawings

NOVEL Δ$^{4,9}$-GONADIENE-21-OL-3,20-DIONES

STATE OF THE ART

Commonly assigned U.S. Pat. No. 3,679,714, French patent No. 2,149,302 and British Pat. No. 902,373 describe related gonane compounds.

OBJECTS OF THE INVENTION

It is an object of the invention to provide the 21R and 21S epimers and mixtures thereof of the compounds of formula I.

It is another object of the invention to provide a novel process for the preparation of compounds of formula I and novel intermediates therefore.

It is a further object of the invention to provide novel progestomimetic and antiestrogenic compositions and to a novel method of inducing progestomimetic and antiestrogenic activity in warm-blooded animals, and to a novel process for localization and dosage of progesterone in warm-blooded animals.

These and other objects and advantages of the invention will become obvious from the following detailed description.

THE INVENTION

The novel Δ$^{4,9}$-gonadiene-21-ol-3,20-diones of the invention have the formula

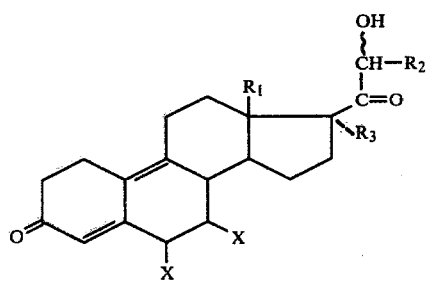

wherein X is selected from the group consisting of hydrogen and tritium, $R_1$ is alkyl of 1 to 3 carbon atoms, $R_2$ is alkyl of 1 to 12 carbon atoms and $R_3$ is alkyl of 1 to 4 carbon atoms in the form of 21R or 21S epimers or mixtures thereof.

Among the preferred compounds of formula I are those wherein X is hydrogen, those wherein $R_1$ is methyl or ethyl, those wherein $R_3$ is methyl, ethyl or n-propyl and those wherein $R_2$ is methyl, ethyl, n-propyl, isopropyl, n-butyl, isobutyl, n-pentyl, n-hexyl, 2-methylpentyl, 2,3-dimethylbutyl, n-octyl or 2,2-dimethylhexyl.

Especially preferred are the compounds of formula I wherein $R_1$ is methyl, those wherein $R_2$ is methyl and those wherein $R_3$ is methyl, each in the form of their 21R or 21S epimers or mixtures of said epimers. Especially preferred are the 21S epimers which are referred to in the Examples as product A.

The novel process of the invention for the preparation of compounds of formula I wherein X is hydrogen comprises reacting a compound of the formula

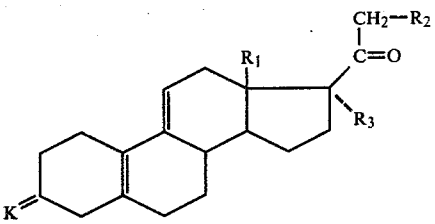

wherein $R_1$, $R_2$ and $R_3$ have the above definitions and K is a ketal with an oxidation agent in the presence of a tertiary alcoholate and then with a reducing agent to form a compound of the formula

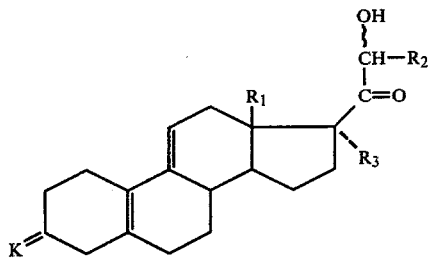

in the form of a mixture of its 21R and 21S epimers and reacting the latter with acid hydrolysis agent capable of hydrolyzing the ketal group and isomerizing the Δ$^{5(10),9(11)}$-double bond system to a Δ$^{4,9}$-system to obtain a compound of formula I wherein X is hydrogen in the form of a mixture of 21R and 21S epimers and optionally separating the mixture into the individual epimers.

K is preferably a cyclic alkyl ketal of 2 to 4 carbon atoms such as ethyleneketal or propyleneketal or a dialkyl ketal such as dimethylketal or diethylketal. The preferred oxidation agent is molecular oxygen and the alkali metal tertiary alcoholate is preferably alkali metal tert.-butylates or teramylates such as sodium, potassium or lithium. The reducing agent is preferably a triloweralkyl phosphite of 1 to 5 alkyl carbon atoms such as trimethylphosphite or triethylphosphite.

The acid hydrolysis agent capable of hydrolyzing the ketal group and isomerizing the Δ$^{5(10),9(11)}$-system is preferably commercial sulfonic acid resins on a support of polystyrene or a styrene-divinylbenzene copolymer but may also be an inorganic acid such as hydrochloric acid or sulfuric acid or p-toluenesulfonic acid or perchloric acid. The epimeric mixtures may be separated by classical methods such as chromatography.

The process of the invention for the preparation of compounds of formula I comprises reacting a compound of the formula

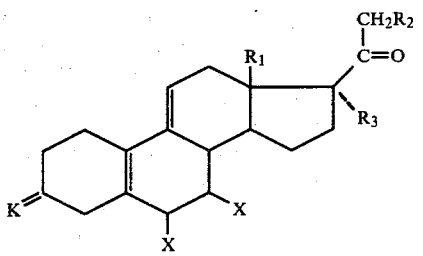

wherein K, X, $R_1$, $R_2$ and $R_3$ have the above definitions with a strong base to form an intermediate enolate, reacting the latter with iodine to obtain a compound of the formula

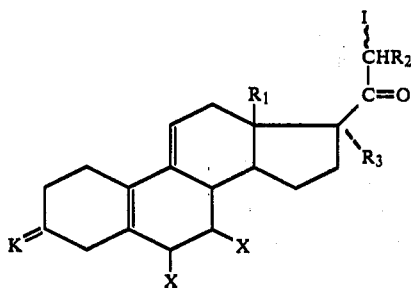

in a mixture of 21R and 21S isomers, reacting the latter with an alkali metal acetate to form a compound of the formula

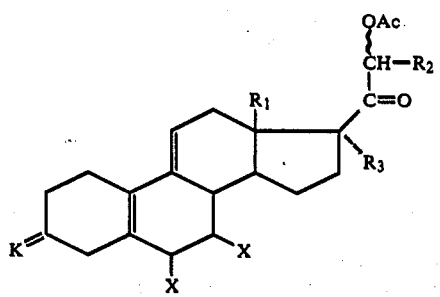

in the form of a mixture of 21R and 21S isomers, reacting the latter with an acid hydrolysis agent capable of hydrolyzing the ketal group and isomerizing the $\Delta^{5(10),9(11)}$-double bond system to a $\Delta^{4,9}$-system to obtain a compound of the formula

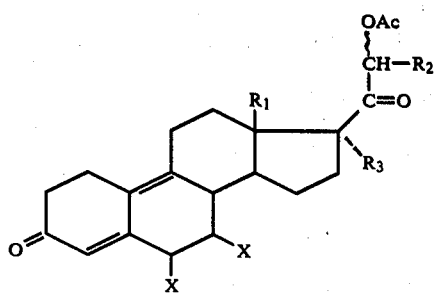

in the form of a mixture of its 21R and 21S isomers and reacting the latter with a saponification agent to obtain the compound of formula I in a mixture of its 21R and 21S isomers which may be separated, if desired.

Preferably, K may have the above values and the strong base is preferably butyllithium in the presence of an amine such as N-cyclohexyl isopropylamine but equally useful are alkali metal hydrides and alkali metal tert-butylates. The preferred alkali metal acetate is sodium acetate or potassium acetate. The acid hydrolysis agent capable of hydrolyzing the ketal and isomerizing the $\Delta^{5(10),9(11)}$-system is that discussed previously. The saponification agent is preferably an alkali metal base such as sodium hydroxide or potassium hydroxide. The separation of the epimers may be effected by classical methods such as chromatography.

The compounds of formulae III, IV, V and VI are novel products. Preferred compounds of formule III are 3-ethylene dioxy 17α methyl-17β-(2-hydroxy-1-oxopropyl) $\Delta^{5(10),9(11)}$ estradiene in the form of their individual epimers or mixtures thereof. Preferred compounds of formule IV are 3-ethylenedioxy-17α-methyl-17β-(2-iodo-1-oxopropyl)-$\Delta^{5(10),9(11)}$-estradiene and [6,7³H]-3-ethylenedioxy-17α-methyl-17β-(2-iodo-1-oxopropyl)-$\Delta^{5(10),9(11)}$-estradiene in the form of individual epimers or mixtures thereof. Preferred compounds of formula V are 3-ethylenedioxy-17α-methyl-17β-(2-acetoxy-1-oxopropyl)-$\Delta^{5(10),9(11)}$-estradiene and [6,7³H] 3-ethylenedioxy-17α-methyl-17β-(2-acetoxy-1-oxopropyl)-$\Delta^{5(10),9(11)}$-estradiene in the form of their individual epimers or mixtures thereof. Preferred compounds of formula VI are 17α-methyl-17β-(2-acetoxy-1-oxopropyl)-$\Delta^{4,9}$-estradiene-3-one and [6,7³H] 17α-methyl-17β-(2-acetoxy-1-oxopropyl)-$\Delta^{4,9}$-estradiene-3-one in the form of their individual epimers or mixtures thereof.

The compounds of formula II are generally known and may be prepared by the process of French pat. No. 2,149,302 for example. The compounds of formula II wherein X is tritium may be prepared by the process U.S. Pat. No. 4,152,325.

The novel progestomimetic and antiestrogenic compositions having progestomimetic and antiestrogenic activity are comprised of a progestomimetically and antiestrogenically effective amount of at least one compound of formula I wherein X is hydrogen and an inert pharmaceutical carrier or excipient. The compositions may be in the form of tablets, dragees, cachets, capsules, granules, emulsions, syrups, suppositories, injectable solutions or suspensions, pomades, creams, gels and aerosol preparations made in the usual manner.

Examples of suitable excipients are talc, arabic gum, lactose, starch, magnesium stearate, cacao butter, aqueous and non-aqueous vehicles, fatty bodies of animal or vegetable origin, paraffinic derivatives, glycols, diverse wetting agents, dispersants or emulsifiers and preservatives.

The compositions are therefore useful as progestative medicaments to inhibit hypophysis of anti-LH predominance or as antiestrogenic agents. They are useful for treating dysmenorrhea, sterility, ovarian dystrophia as well for resting the ovaries, treatment of tumors of the uterus and as contraceptives. Particularly preferred are the compounds with the 21-hydroxyl group in the S position.

The novel method of the invention for inducing progestomimetic and antiestrogenic activity in warm-blooded animals, including humans, comprises administering to warm-blooded animals a progestomimetically and antiestrogenically effective amount of at least one compound of formula I wherein X is hydrogen. The compounds may be administered orally, rectally, parenterally or topically to the skin or mucous and the usual daily dose depending upon the compound and the method of administration may be $2.10^{-4}$ to 1 mg/kg, when administered orally in the adult woman.

Another facet of the invention are the compositions for the dosage and localization of specific progesterone receptors comprised of an effective amount of at least one compound of formula I wherein X is tritium and a carrier. The said compounds of formula I have a specific activity on the order of 50 Ci/mM and especially preferred are the 21S isomers.

The compositions are useful especially in uterine cytosol or tumoral cellular cytoplasm (breast cancer) and tumors induced by 9,10-dimethyl-1,2-benzanthracene (DMBA) in the rat. The said compounds of formula I have the advantage over progesterone that they are not fixed by transcortine and have an affinity 2 to 10 times greater than that of progesterone.

The novel process of the invention for localization and dosage of progesterone in warm-blooded animals comprises administering to warm-blooded animals a sufficient amount of at least one compound of formula I wherein X is tritium for localization and dosage of progesterone specific receptors which includes uterine cytosol, breast cancer and tumors induced by DMBA in the rat. The usual procedures are described in numerous publications such as Raynaud et al [Steroids, July 1973, p. 89–97].

In the following examples there are described several preferred embodiments to illustrate the invention. However, it should be understood that the invention is not intended to be limited to the specific embodiments.

EXAMPLE 1

17α-methyl-17β-(2-hydroxy-1-oxopropyl)-$\Delta^{4,9}$-estradiene-3-one

STEP A:
3-(ethylenedioxy)-17α-methyl-17β-(2-hydroxy-1-oxopropyl)-$\Delta^{5(10),9(11)}$-estradiene Oxygen was bubbled at −20° C. through a solution of 907 mg of potassium tert.-butylate, 0.852 ml of triethylphosphite and 13.6 ml of dimethylformamide and then a solution of 1 g of 3-ethylenedioxy-17α-methyl-17β-(1-oxopropyl)$\Delta^{5(10),9(11)}$-estradiene- in 10 ml of dimethylformamide was slowly added thereto at −20° C. while bubbling oxygen therethrough. The mixture stood at −20° C. for 30 minutes and then water was added thereto. The pH of the mixture was adjusted to 5.6 by addition of N hydrochloric acid and the mixture was extracted 5 times with 150 ml of isopropyl ether. The ether phase was dried, filtered and evaporated to dryness to obtain 1.554 g of 3-(ethylenedioxy)-17α-methyl-17β-(2-hydroxy-1-oxopropyl)-$\Delta^{5(10),9(11)}$-estradiene which was used as is for the next step.

STEP B:
17α-methyl-17β-(2-hydroxy-1-oxopropyl)-$\Delta^{4,9}$-estradiene-3-one A mixture of 750 mg of Redex CF resin, 8 ml of 95% ethanol and 510 mg of the product of Step A was refluxed for 7 hours and was filtered. The resin was rinsed with ethanol, then with methylene chloride and the filtrate was evaporated to dryness under reduced pressure to obtain 474 g of a resin. The latter was chromatographed over silica gel and was eluted with a 9–1 methylene chloride-acetone mixture to obtain a mixture of 2 epimers at the 21-position of 17α-methyl-17β-(2-hydroxy-1-oxopropyl)-$\Delta^{4,9}$-estradiene-3-one. The epimers were separated by high pressure liquid chromatography in 400 mm long silica gel columns (5μ silica) with an internal diameter of 6 mm. The eluant was a 7-3 methylene chloride-ethyl acetate mixture with a discharge rate of 160 ml per hour and the UV detector=305 nm. The product which was retained for 19 minutes was product A and the product retained for 17 minutes was product B. The mass spectrum of both showed a molecular peak at 342.

RMN Spectrum (CDCl$_3$): Product A peaks at 5.70 ppm (ethylenic H$_4$); at 0.84 ppm (13-methyl); at 4.33 ppm -multiplets (21-hydrogen); at 1.27 and 1.38 ppm (22-methyl doublets); at 1.18 ppm (17α-methyl).

RMN Spectrum (CDCl$_3$): Product B peaks at 5.70 ppm (ethylenic H$_4$); at 0.81 ppm (13-methyl); at 4.38, 4.50, 4.61 and 4.73 ppm (21-hydrogen); at 1.26 and 1.37 ppm (22-methyl); at 1.16 ppm (17α-methyl).

EXAMPLE 2

A and B isomers of 17α-methyl-17β-(2-hydroxy-1-oxopropyl)-$\Delta^{4,9}$-estradiene-3-one

STEP A: isomeric mixture of 3-ethylenedioxy-17α-methyl-17β-(2-iodo-1-oxopropyl)-$\Delta^{5(10),9(11)}$-estradiene 23,3 ml of butyllithium in hexane were added at −40° C. under an inert atmosphere to a solution of 11.1 ml of N-cyclohexylisopropylamine in 145 ml of tetrahydrofuran and after stirring the mixture for 5 minutes, 10.3 g of 3-ethylenedioxy-17α-methyl-17β-(1-oxopropyl)-$\Delta^{5(10),9(11)}$-estradiene were added thereto. The mixture was stirred for 20 minutes at 40° C. and was then cooled to −50° C. A solution of 8.2 g of iodine in 60 ml of tetrahydrofuran was added thereto over 5 minutes and the mixture was stirred at −50° C. for 5 minutes. The temperature was allowed to rise to room temperature and the mixture was poured into 100 ml of aqueous saturated ammonium chloride solution. The mixture was extracted with ether and the ether phase was washed aqueous 10% sodium thiosulfate solution, then with water, dried and evaporated to dryness under reduced pressure to obtain 14.5 g of isomeric mixture of 3-ethylenedioxy-17α-methyl-17β-(2-iodo-1-oxopropyl)-$\Delta^{5(10),9(11)}$-estradiene which was used as is for the next step.

STEP B: isomeric mixture of 3-ethylenedioxy-17α-methyl-17β-(2-acetoxy-1-oxopropyl)-$\Delta^{5(10),9(11)}$-estradiene A mixture of 14.9 g of the product of Step A, 29 g of anhydrous potassium acetate and 50 ml of dimethylformamide was stirred at 80° C. under an inert atmosphere for one hour and was then poured into 300 ml of water. The mixture was extracted with ether and the ether phase was washed with water, dried and evaporated to dryness under reduced pressure to obtain 11.8 g of isomeric mixture of 3-ethylenedioxy-17α-methyl-17β-(2-acetoxy-1-oxopropyl)-$\Delta^{5(10),9(11)}$-estradiene.

STEP C: isomeric mixture of 17α-methyl-17β-(2-acetoxy-1-oxopropyl)-$\Delta^{4,9}$-estradiene-3-one A solution of 11.8 g of the product of Step B, 110 ml of acetic acid and 11 ml of perchloric acid was stirred under an inert atmosphere at room temperature for one hour and 400 ml of water were added thereto. The mixture was extracted with methylene chloride and the organic phase was washed with aqueous saturated sodium bicarbonate solution, dried and evaporated to dryness under reduced pressure to obtain 12 g of residue. The latter was chromatographed over silica gel and was eluted with an 8-2 benzene-ethyl acetate mixture to obtain 8.6 g of isomeric mixture of 17α-methyl-17β-(2-acetoxy-1-oxopropyl)-Δ$^{4,9}$-estradiene-3-one which was used as is for the next step.

STEP D: A and B isomers of 17α-methyl-17β-(2-hydroxy-1-oxopropyl)-Δ$^{4,9}$-estradiene-3-one 86 mg of potassium hydroxide were added under an inert atmosphere to a solution of 8.6 g of the product of Step C in 50 ml of methanol and the mixture was stirred at room temperature for 5 hours. 50 ml of 0.1 N hydrochloric acid were added to the mixture which was then extracted with methylene chloride. The organic phase was dried and evaporated to dryness under reduced pressure. The 7.6 g of residue were chromatographed over silica gel and were eluted with an 8-2 benzene-ethyl acetate mixture to obtain 2.7 g of isomer B and 2.5 g of isomer A of 17α-methyl-17β-(2-hydroxy-1-oxopropyl)-Δ$^{4,9}$-estradiene-3-one. The isomer B was crystallized from ether and then from ethanol to obtain 1.3 g of product melting at 190° C. and a specific rotation of $[\alpha]_D^{20} = -345° \pm 4.5°$ (c=1% in CHCl$_3$). Crystallization of isomer A from ether yielded 1.2 g of product melting at 122° C. and a specific rotation of $[\alpha]_D^{20} = -208° \pm 3°$ (c=1% in CHCl$_3$).

Analysis: Isomer B Calculated: %C 77.15; %H 8.83; Found: %C 77.2; %H 9.0.

RMN Spectrum (CDCl$_3$):

quintuplet at 4.58 ppm, J=7 (2-hydrogen of propyl); at 1.27-1.38 ppm (3-hydrogens of propyl); at 1.17 ppm (hydrogens of 17α-methyl); at 0.82 ppm (hydrogens of 18-methyl).

Analysis: Isomer A Calculated: %C 77.15; %H 8.83; Found: %C 77.2; %H 9.1.

RMN Spectrum (CDCl$_3$):

quadruplet at 4.2 to 4.67 ppm (2-hydrogen of propyl); at 1.18 ppm (hydrogens of 17α-methyl); at 0.84 ppm (hydrogens of 18-methyl). Analysis by circular dichroism and X-ray diffraction determined that isomer B had a 21R configuration and isomer A had a 21S configuration.

EXAMPLE 3

A and B isomers of [6,7$^3$H] 17α-methyl-17β-(2-hydroxy-1-oxopropyl)-Δ$^{4,9}$-estradiene-3-one A mixture of 23.8 mg of [6,7$^3$H] 17α-methyl-17β-(1-oxopropyl)-Δ$^{4,9}$-estradiene-3-one (described in French published patent application No. 2,374,335), 2 ml of methylene glycol containing 1 mg of p-toluene sulfonic acid and 1 ml of ethyl orthoformate was stirred under an inert atmosphere and was then heated at 60° C. for 10 minutes. Triethylamine was added to the mixture which was then cooled and aqueous saturated sodium bicarbonate solution was added thereto. The mixture was extracted with ethyl acetate and the organic phase was washed with aqueous sodium chloride, dried and evaporated to dryness. The residue was pressure chromatographed over silica gel and was eluted with a 9-1 benzene-ethyl acetate mixture containing 0.5% of triethylamine to obtain a mixture of the A and B isomers of [6,7$^3$H] 3-ethylenedioxy-17α-methyl-17β-(1-oxopropyl)-Δ$^{5(10),9(11)}$-estradiene.

Using the procedure of Step A of Example 2, 17.5 mg of [6,7$^3$H] 3-ethylenedioxy-17α-methyl-17β-(1-oxopropyl)-Δ$^{5(10),9(11)}$-estradiene were reacted to obtain mixture of isomers of [6,7$^3$H] 3-ethylenedioxy-17α-methyl-17β-(2-iodo-1-oxopropyl)-Δ$^{5(10),9(11)}$-estradiene in the form of a resin. The latter was immediately reacted as in Step B of Example 2 and extraction with ethyl acetate containing 0.1% of triethylamine yielded an isomer mixture of [6,7$^3$H] 3-ethylenedioxy-17α-methyl-17β-(2-acetoxy-1-oxopropyl)-Δ$^{5(10),9(11)}$-estradiene. The said compound was reacted as in Step C of Example 2 to obtain an isomeric mixture of [6,7$^3$H] 17α-methyl-17β-(2-acetoxy-1-oxopropyl)-Δ$^{4,9}$-estradiene-3-one in the form of an resin. The said product was then reacted as in Step D of of Example 2 to obtain 2.64 mg of isomer B (21R) and 1.69 mg of isomer A (21S) of [6,7$^3$H] 17α-methyl-17β-(2-hydroxy-1-oxopropyl)-Δ$^{4,9}$-estradiene-3-one.

EXAMPLE 4

Tablets were prepared containing 100 μg of the compound of Example 1 and sufficient excipient of talc, starch and magnesium stearate for a final tablet weight of 100 mg.

PHARMACOLOGICAL STUDY

A. Progestomimetic Activity

The progestomimetic activity was determined for the product A of Example 1 by the hormonal receptor method of Raynaud et al [J. Ster. Biochem., Vol. 6 (1975), p. 615-622 and Physiology and Genetics of Reproduction, 1975, Part A, p. 143-160]. Immature rabbits received 25 μg of estradiol percutaneously and were sacrificed after 5 days and the uterus was removed and homogenized in a buffered solution of 10 mM of tromethamine, 0.25 M of saccharose and a pH of 7.4 was kept with hydrochloric acid. The homogenate was centrifuged at 105,000 g per hour and the surnageant or cytosol was adjusted to a solution of 1/50 (weight/volume). The resulting solution was incubated at 0° C. for 2 hours in tubes with the same volume of cytosol with a fixed concentration of tritiated 17,21-dimethyl-19-nor-Δ$^{4,9}$-pregnadiene-3,20-dione (designated at tritiated Product R) in the presence or not of an increasing concentration of radio-inactive 17,21-dimethyl-19-nor-Δ$^{4,9}$-pregnadiene-3,20-dione (designated as cold product R) or progesterone or the test product. The radioactivity of the tritiated product R was determined after 2 hours and after 24 hours by the technique of adsorption on carbon-dextran (1.25%-0.625%). The plots were the curves of the right parallel of the axis of abscisses of ordinate $$I_{50} = \frac{100 \left(1 + \frac{Bmin}{Bo}\right)}{2}$$

wherein Bo is the maximum amount of tied tritiated product R measured in the incubation containing only tritiated product R and Bmin is the minimum amount of tied tritiated product R (non-specific) measured in the incubation containing tritiated product R and a large excess of cold product R ($2500 \times 10^{-9}$ M) and the curves representing the percentages of tied tritiated product R B/Bo as a logarithmatic function of the concentrations of added cold product R.

The intersections of these $I_{50}$ straight lines and the curves permit the determination of the values: CP—concentration of cold progesterone which inhibits by 50% the fixation of the tritiated product R and CX—concentration of test product which inhibits by 50% the fixation of tritiated product R. The relative affinity of the test product (ARL) was determined by the formula $$ARL = 100 \times \frac{CP}{CX}$$

and the results are reported in Table I

TABLE I

| Product | ARL | |
|---|---|---|
| | 2 h | 24 h |
| Progesterone | 100 | 100 |
| Product A of Example 1 | 204 | 688 |

The results of Table I show that the product A of Example 1 has a much greater affinity for specific uterine reception of progesterone than progesterone which means the product has progestomimetic activity.

B. Progestomimetic Activity

The progestomimetic activity was also determined by the Clauberg test in which groups of 3 immature rabbits were previously sensitized by subcutaneous administration of estradiol for 5 days at a daily dose of 5 μg. Two days after the last treatment, the compound A of Example 1 in solution in sesame oil containing 5% of benzyl alcohol was subcutaneously administered daily for 5 days and the rabbits were killed on the 6th day. The uterus was removed and the proliferation of endometric lace which is characteristic of progestomimetic activity was determined in MacPhail units. The results are in Table II.

TABLE II

| Dose of Product A of Example 1, μg daily doses | MacPhail units |
|---|---|
| 1 | 2.2 |
| 3 | 3.4 |
| 10 | 3.4 |

The results of Table II shows that the tested compound has a very strong progestomimetic activity since it shows 2.2 MacPhail units at a daily dose of 1 μg.

C. Antiestrogenic Activity

The estrogenic activity of the product A of Example 1 was also determined by the method of Rubin [Endocrinology, Vol. 49 (1951), p. 429] and Dorfman et al [Methods in Hormone Research, Vol. II (1962), p. 118] in which groups of 4 immature female mice 18 days old received once a day for 3 days a subcutaneous injection of estradiol only, only the test product or estradiol and the test product. In the last case, separate injections were used. The animals were killed on the 4th day and the uterus was removed, dissected and weighed. The test product was administered in a volume of 0.1 ml of sesame oil solution containing 5% of benzyl alcohol at a total dose of 0.27 μg of estradiol and the test compound was used at total doses of 0.3, 1.0, 3 and 10 μg. The results are reported in Table III.

TABLE III

| Lots | Total Dose μg | Average Weight of uterus in mg |
|---|---|---|
| Controls | 0 | 14.4 |
| Estradiol | 0.27 | 99.3 |
| Product A | 0.3 | 14.6 |
| Product A + Estradiol | 0.3 + 0.27 | 80.5  −19% |
| Product A | 1 | 13.0 |
| Product A + Estradiol | 1 + 0.27 | 59.6  −39% |
| Product A | 3 | 17.1 |
| Product A + Estradiol | 3 + 0.27 | 38.5  −61% |
| Product A | 10 | 15.8 |
| Product A + Estradiol | 10 + 0.27 | 39.6  −60% |

The results of Table III show that the compound A of Example 1 has a clear antiestrogenic activity against estradiol at a dose of 1 μg.

Various modifications of the products and process of the invention may be made without departing from the spirit or scope thereof and it is to be understood that the invention is intended to be limited only as defined in the appended claims.

I claim:

1. A $\Delta^{4,9}$-gonadiene-3,20-dione of the formula

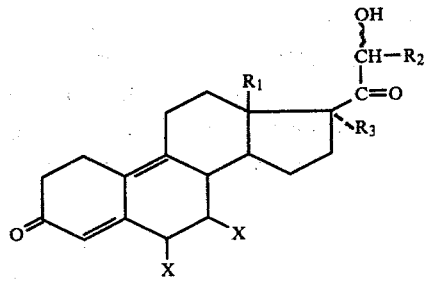

wherein X is selected from the group consisting of hydrogen and tritium, $R_1$ is alkyl of 1 to 3 carbon atoms, $R_2$ is alkyl of 1 to 12 carbon atoms and $R_3$ is alkyl of 1 to 4 carbon atoms in the form of 21R or 21S epimers or mixtures thereof.

2. A compound of claim 1 wherein X is hydrogen.
3. A compound of claim 1 wherein $R_1$ is methyl.
4. A compound of claim 1 wherein $R_2$ is methyl.
5. A compound of claim 1 wherein $R_3$ is methyl.
6. A compound of claim 1 selected from the group consisting of 17α-methyl-17β-(2-hydroxy-1-oxo-propyl)-$\Delta^{4,9}$-estradiene-3-one and [6,7³H] 17α-methyl-17β-(2-hydroxy-1-oxo-propyl)-$\Delta^{4,9}$-estradiene-3-one in the form of their individual 21R and 21S epimers or mixtures thereof.

7. A process for the preparation of a compound of claim 1 wherein X is hydrogen comprising reacting a compound of the formula

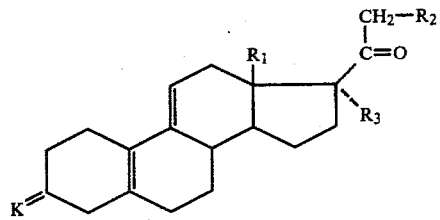

wherein $R_1$, $R_2$ and $R_3$ have the above definitions and K is a ketal with molecular oxygen in the presence of a tertiary alcoholate and then with a triloweralkyl-phosphite reducing agent of 1 to 5 alkyl carbon atoms to form a compound of the formula

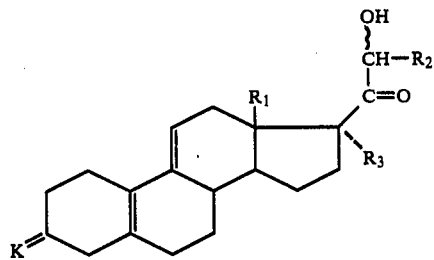

in the form of a mixture of its 21R and 21S epimers and reacting the latter with acid hydrolysis agent capable of hydrolyzing the ketal group and isomerizing the $\Delta^{5(10),9(11)}$-system to a $\Delta^{4,9}$-system selected from the group consisting of sulfonic acid resins, inorganic acids, p-toluene sulfonic acid and perchloric acid to obtain a compound of claim 1 wherein X is hydrogen in the form of a mixture of 21R and 21S epimers and optionally separating the mixture into the individual epimers.

8. A process for the preparation of a compound of claim 1 comprising reacting a compound of the formula

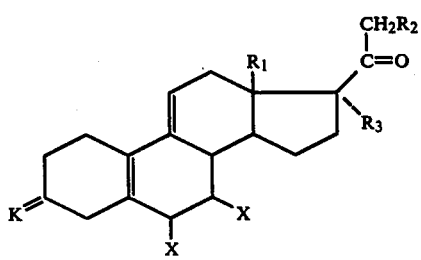

wherein K, $R_1$, $R_2$ and $R_3$ have the above definitions with a strong base and then with iodine to obtain a compound of the formula

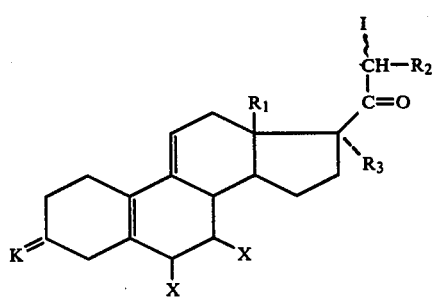

in a mixture of 21R and 21S isomers, reacting the latter with an alkali metal acetate to form a compound of the formula

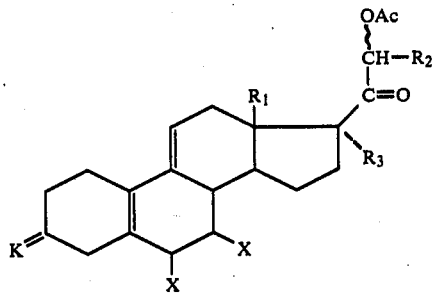

in the form of a mixture of 21R and 21S isomers, reacting the latter with an acid hydrolysis agent capable of hydrolyzing the ketal group and isomerizing the $\Delta^{5(10),9(11)}$-double bond system to a $\Delta^{4,9}$-system selected from the group consisting of sulfonic acid resins, inorganic acids, p-toluene sulfonic acid and perchloric acid to obtain a compound of the formula

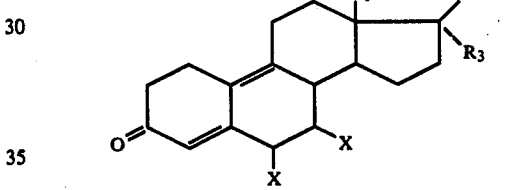

in the form of a mixture of its 21R and 21S isomers and reacting the latter with a saponification agent to obtain the compound of claim 1 in a mixture of its 21R and 21S isomers which may be separated, if desired.

9. A compound selected from the formulae of the group consisting of

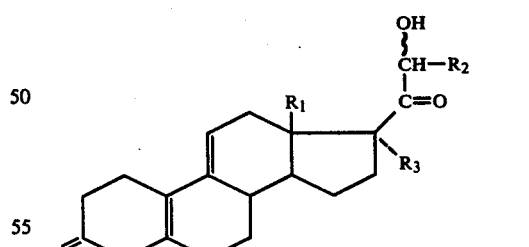

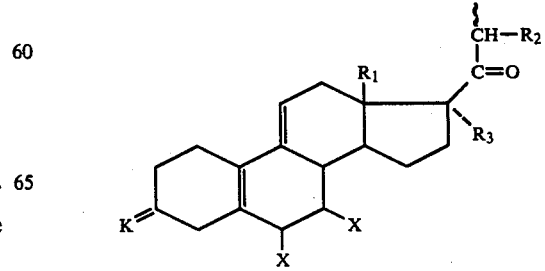

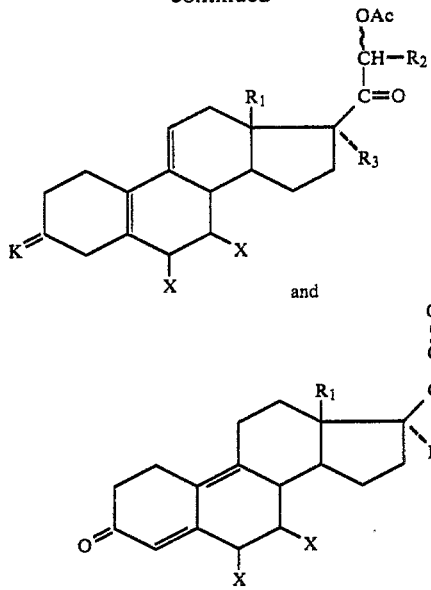

wherein X is selected from the group consisting of hydrogen and tritium, K is selected from the group consisting of dialkyl ketal and alkylenedioxy of 2 to 4 carbon atoms, $R_1$ is alkyl of 1 to 3 carbon atoms, $R_2$ is alkyl of 1 to 12 carbon atoms, $R_3$ is alkyl of 1 to 4 carbon atoms and QAc is acetoxy in the form of their individual 21R and 21S epimers or mixtures thereof.

10. A compound of claim 9 selected from the group consisting of 3-ethylenedioxy-17α-methyl-17β-(2-hydroxy-1-oxopropyl)-$\Delta^{5(10),9(11)}$-estradiene, $[6,7^3H]$ 3-ethylenedioxy-17α-methyl-17β-(2-iodo-1-oxopropyl)-$\Delta^{5(10),9(11)}$-estradiene, 3-ethylenedioxy-17α-methyl-17β-(2-iodo-1-oxopropyl)-$\Delta^{5(10),9(11)}$-estradiene, 3-ethylenedioxy-17α-methyl-17β-(2-acetoxy-1-oxopropyl)-$\Delta^{5(10),9(11)}$-estradiene, $[6,7^3H]$ 3-ethylenedioxy-17α-methyl-17β-(2-acetoxy-1-oxopropyl)-$\Delta^{5(10),9(11)}$-estradiene, 17α-methyl-17β-(2-acetoxy-1-oxopropyl)-$\Delta^{4,9}$-estradiene-3-one and $[6,7^3H]$ 17α-methyl-17β-(2-acetoxy-1-oxopropyl)-$\Delta^{4,9}$-estradiene-3-one.

11. A progestomimetic composition having antiestrogenic activity comprising a progestomimetically effective amount of at least one compound of claim 1 and a pharmaceutical carrier.

12. A composition of claim 11 wherein X is hydrogen.

13. A composition of claim 11 wherein $R_1$ is methyl.

14. A composition of claim 11 wherein $R_2$ is methyl.

15. A composition of claim 11 wherein $R_3$ is methyl.

16. A composition of claim 11 selected from the group consisting of 17α-methyl-17β-(2-hydroxy-1-oxopropyl)-$\Delta^{4,9}$-estradiene-3-one and $[6,7^3H]$-17α-methyl-17β-(2-hydroxy-1-oxopropyl)-$\Delta^{4,9}$-estradiene-3-one in the form of their individual 21R and 21S epimers or mixutres thereof.

17. A method of inducing progestomimetic and antiestrogenic activity in warm-blooded animals comprising administering to warm-blooded animals a progestomimetically and antiestrogenically effective amount of at least one compound of claim 1, wherein X is hydrogen.

18. A method of claim 17 wherein $R_1$ is methyl.

19. A method of claim 17 wherein $R_2$ is methyl.

20. A method of claim 17 wherein $R_3$ is methyl.

21. A method of claim 17 wherein the compound is selected from the group consisting of 17α-methyl-17β-(2-hydroxy-1-oxopropyl)-$\Delta^{4,9}$-estradiene-3-one in the form of its individual 21R and 21S epimers or mixtures thereof.

22. A method of inducing contraceptive activity in warm-blooded female animals comprising administering to warm-blooded female animals an amount of at least one compound of claim 1 wherein X is hydrogen sufficient to prevent conception.

23. A method of localization and dosage of progesterone specific receptors in warm-blooded animals comprising administering to warm-blooded animals a sufficient amount of at least one compound of claim 1 wherein X is tritium for localization and dosage of progesterone specific receptors.

24. A method of claim 23 wherein the compound is selected from the group consisting of $(6,7^3H)$ 17α-methyl-17β-(2-hydroxy-1-oxopropyl)-$\Delta^{4,9}$-estradiene-3-one in the form of its individual 21R and 21S epimers or mixtures thereof.

* * * * *